United States Patent
Kanca

(10) Patent No.: US 7,074,040 B2
(45) Date of Patent: Jul. 11, 2006

(54) BALL LENS FOR USE WITH A DENTAL CURING LIGHT

(75) Inventor: John Kanca, Middleberry, CT (US)

(73) Assignee: Ultradent Products, Inc., South Jordan, UT (US)

( * ) Notice: Subject to any disclaimer, the term of this patent is extended or adjusted under 35 U.S.C. 154(b) by 69 days.

(21) Appl. No.: 10/813,306

(22) Filed: Mar. 30, 2004

(65) Prior Publication Data

US 2005/0221250 A1    Oct. 6, 2005

(51) Int. Cl.
*A61C 1/00* (2006.01)
*A61C 3/08* (2006.01)

(52) U.S. Cl. ....................................... 433/29
(58) Field of Classification Search ............ 433/29, 433/164; 606/17
See application file for complete search history.

(56) References Cited

U.S. PATENT DOCUMENTS

| | | |
|---|---|---|
| 3,310,358 A | 3/1967 | Marcatili |
| 3,704,928 A | 12/1972 | Coombs et al. |
| 3,930,149 A | 12/1975 | French |
| 4,184,196 A | 1/1980 | Moret |
| 4,221,994 A | 9/1980 | Friedman et al. |
| 4,229,658 A | 10/1980 | Gonser |
| 4,245,890 A | 1/1981 | Hartman et al. |
| 4,281,366 A | 7/1981 | Wurster et al. |
| 4,309,617 A | 1/1982 | Long |
| 4,348,180 A | 9/1982 | Schuss |
| 4,385,344 A | 5/1983 | Gonser ............. 362/32 |
| 4,392,827 A | 7/1983 | Martin |
| 4,522,594 A | 6/1985 | Stark et al. |
| 4,611,992 A | 9/1986 | Lokken |
| 4,666,405 A * | 5/1987 | Ericson ............. 433/229 |
| 4,666,406 A | 5/1987 | Kanca, III |
| 4,682,950 A | 7/1987 | Dragan |
| 4,698,730 A | 10/1987 | Sakai et al. |
| 4,733,937 A | 3/1988 | Lia et al. |
| 4,836,782 A | 6/1989 | Gonser |
| 4,935,665 A | 6/1990 | Murata |
| 4,948,215 A | 8/1990 | Friedman |
| 4,963,798 A | 10/1990 | McDermott |
| 5,013,144 A | 5/1991 | Silverglate et al. |
| 5,013,240 A | 5/1991 | Bailey et al. |
| 5,043,634 A | 8/1991 | Rothwell, Jr. et al. |
| 5,046,810 A * | 9/1991 | Steiner et al. ............. 385/38 |
| 5,071,222 A | 12/1991 | Laakmann et al. |
| 5,115,761 A | 5/1992 | Hood |
| 5,123,845 A | 6/1992 | Vassiliadis et al. |
| 5,139,495 A | 8/1992 | Daikuzono |
| 5,161,879 A | 11/1992 | McDermott |

(Continued)

OTHER PUBLICATIONS

3M ESPE, "Elipar™ Freelight" "LED Curing Light" Technical Product Profile.

(Continued)

*Primary Examiner*—Cary E. O'Connor
*Assistant Examiner*—Patrick J. Kilkenny
(74) *Attorney, Agent, or Firm*—Workman Nydegger

(57) ABSTRACT

A ball lens includes a connector body that couples or attaches to a dental curing light so as to capture at least some of the light emitted by the light source, an elongate light guide extending from the connector body, and a light-emitting ball at an end of the light guide distal to the connector body. The ball can be used to hold a matrix band against an adjacent tooth prior to and/or while incrementally curing a light curable composition.

24 Claims, 10 Drawing Sheets

U.S. PATENT DOCUMENTS

| | | |
|---|---|---|
| 5,275,564 A | 1/1994 | Vassiliadis et al. |
| 5,285,318 A | 2/1994 | Gleckman |
| 5,288,231 A | 2/1994 | Kuehn et al. |
| 5,290,169 A | 3/1994 | Friedman et al. |
| 5,312,249 A | 5/1994 | Kennedy |
| 5,328,368 A | 7/1994 | Lansing et al. |
| 5,348,552 A | 9/1994 | Nakajima et al. |
| 5,382,799 A | 1/1995 | May |
| 5,388,988 A | 2/1995 | Goisser et al. |
| 5,397,892 A | 3/1995 | Abdelqader |
| 5,415,543 A | 5/1995 | Rozmajzl, Jr. |
| 5,420,768 A | 5/1995 | Kennedy |
| D361,382 S | 8/1995 | Brunsell et al. |
| 5,448,323 A | 9/1995 | Clark et al. |
| 5,457,611 A | 10/1995 | Verderber |
| 5,485,317 A | 1/1996 | Perissinotto et al. |
| 5,521,392 A | 5/1996 | Kennedy et al. |
| 5,527,261 A | 6/1996 | Monroe et al. |
| 5,616,141 A | 4/1997 | Cipolla |
| 5,634,711 A | 6/1997 | Kennedy et al. |
| 5,660,461 A | 8/1997 | Ignatius et al. |
| 5,669,769 A | 9/1997 | Disel |
| D385,051 S | 10/1997 | Wu |
| D385,360 S | 10/1997 | Lieb et al |
| 5,698,866 A | 12/1997 | Doiron et al. |
| 5,711,665 A | 1/1998 | Adam et al. |
| 5,733,029 A | 3/1998 | Monroe |
| 5,749,724 A * | 5/1998 | Cheng .................. 433/29 |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott |
| 5,784,508 A * | 7/1998 | Turner ..................... 385/31 |
| 5,791,898 A * | 8/1998 | Maissami ................. 433/164 |
| 5,797,740 A | 8/1998 | Lundvik |
| 5,803,729 A | 9/1998 | Tsimerman |
| 5,880,839 A | 3/1999 | Ishizuka et al. |
| 5,885,082 A | 3/1999 | Levy |
| 5,897,314 A * | 4/1999 | Hack et al. ................. 433/29 |
| 5,905,268 A | 5/1999 | Garcia et al. |
| 5,908,294 A | 6/1999 | Schick et al. |
| 5,908,295 A | 6/1999 | Kawata |
| 5,921,777 A | 7/1999 | Dorman |
| 5,971,755 A * | 10/1999 | Liebermann et al. ......... 433/29 |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,599 A | 2/2000 | Völcker et al. |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. |
| 6,155,823 A | 12/2000 | Nagel |
| 6,159,005 A | 12/2000 | Herold et al. |
| 6,200,134 B1 | 3/2001 | Kovac et al. |
| 6,208,788 B1 | 3/2001 | Nosov |
| 6,270,343 B1 | 8/2001 | Martin |
| 6,280,187 B1 | 8/2001 | Stone |
| 6,282,013 B1 | 8/2001 | Ostler et al. |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 | 12/2001 | Cao |
| 6,361,192 B1 | 3/2002 | Fussell et al. |
| 6,361,489 B1 | 3/2002 | Tsai |
| 6,379,347 B1 * | 4/2002 | Maki et al. .................. 606/17 |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 * | 7/2002 | Adam et al. .................. 433/29 |
| 6,439,888 B1 | 8/2002 | Boutoussov et al. |
| 6,465,961 B1 | 10/2002 | Cao |
| 6,468,077 B1 | 10/2002 | Melikechi et al. |
| 6,478,447 B1 | 11/2002 | Yen |
| 6,482,004 B1 * | 11/2002 | Senn et al. .................. 433/29 |
| 6,485,301 B1 | 11/2002 | Gemunder et al. |
| 6,511,317 B1 | 1/2003 | Melikechi et al. |
| 6,511,321 B1 | 1/2003 | Trushkowsky et al. |
| 6,514,075 B1 | 2/2003 | Jacob |
| 6,562,029 B1 * | 5/2003 | Maki et al. .................. 606/17 |
| 6,579,286 B1 * | 6/2003 | Maki et al. .................. 606/17 |
| 6,607,384 B1 * | 8/2003 | Nakanishi .................. 433/29 |
| 6,607,526 B1 * | 8/2003 | Maki .......................... 606/16 |
| 6,611,110 B1 | 8/2003 | Fregoso |
| 6,620,154 B1 * | 9/2003 | Amirkhanian et al. ........ 606/17 |
| 6,666,875 B1 | 12/2003 | Sakurai et al. .............. 606/169 |
| 6,692,251 B1 * | 2/2004 | Logan et al. ................. 433/29 |
| 6,692,252 B1 | 2/2004 | Scott |
| 6,709,128 B1 | 3/2004 | Gordon et al. |
| 6,719,558 B1 | 4/2004 | Cao |
| 6,719,559 B1 | 4/2004 | Cao |
| 6,755,648 B1 | 6/2004 | Cao |
| 6,755,649 B1 | 6/2004 | Cao |
| 6,878,145 B1 * | 4/2005 | Brugger et al. ............... 606/18 |
| 2001/0038992 A1 | 11/2001 | Otsuka |
| 2001/0046652 A1 | 11/2001 | Ostler et al. |
| 2001/0055451 A1 | 12/2001 | Kuhara et al. |
| 2002/0028419 A1* | 3/2002 | Slone ......................... 433/29 |
| 2002/0073921 A1 | 6/2002 | Russell et al. |
| 2002/0085372 A1 | 7/2002 | Lehrer |
| 2002/0093833 A1 | 7/2002 | West |
| 2002/0102513 A1* | 8/2002 | Plank ......................... 433/29 |
| 2002/0115037 A1 | 8/2002 | Cao |
| 2002/0133970 A1 | 9/2002 | Gordon et al. |
| 2002/0147383 A1 | 10/2002 | Weber et al. |
| 2002/0163317 A1 | 11/2002 | Cao |
| 2002/0167283 A1 | 11/2002 | Cao |
| 2002/0168306 A1 | 11/2002 | Cao |
| 2002/0168603 A1 | 11/2002 | Cao ............................ 433/29 |
| 2002/0168604 A1 | 11/2002 | Cao |
| 2002/0168605 A1 | 11/2002 | Cao |
| 2002/0168606 A1 | 11/2002 | Cao |
| 2002/0168607 A1 | 11/2002 | Cao |
| 2002/0168608 A1 | 11/2002 | Cao |
| 2002/0172912 A1 | 11/2002 | Cao |
| 2002/0172913 A1 | 11/2002 | Cao |
| 2002/0172914 A1 | 11/2002 | Cao |
| 2002/0172915 A1 | 11/2002 | Cao |
| 2002/0172916 A1 | 11/2002 | Cao |
| 2002/0172917 A1 | 11/2002 | Cao |
| 2002/0175352 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0182561 A1 | 12/2002 | Cao |
| 2002/0182562 A1 | 12/2002 | Cao |
| 2002/0187454 A1 | 12/2002 | Melikechi et al |
| 2002/0187455 A1* | 12/2002 | Melikechi et al. ............ 433/29 |

| | | |
|---|---|---|
| 2002/0190659 A1 | 12/2002 | Cao |
| 2002/0190660 A1 | 12/2002 | Cao |
| 2002/0197582 A1* | 12/2002 | Cao .......................... 433/29 |
| 2003/0001507 A1 | 1/2003 | Cao |
| 2003/0036031 A1* | 2/2003 | Lieb et al. .................... 433/29 |
| 2003/0038291 A1 | 2/2003 | Cao |
| 2003/0039119 A1 | 2/2003 | Cao |
| 2003/0039120 A1 | 2/2003 | Cao |
| 2003/0039122 A1 | 2/2003 | Cao |
| 2003/0040200 A1 | 2/2003 | Cao |
| 2003/0081430 A1* | 5/2003 | Becker ....................... 362/573 |
| 2003/0133203 A1 | 7/2003 | McLean et al. |
| 2003/0133298 A1 | 7/2003 | Cao |
| 2003/0142413 A1 | 7/2003 | McLean et al. |
| 2003/0147254 A1 | 8/2003 | Yoneda et al. |
| 2003/0147258 A1 | 8/2003 | Fischer et al. |
| 2003/0148242 A1 | 8/2003 | Fischer et al. ................ 433/29 |
| 2003/0152885 A1 | 8/2003 | Dinh |
| 2003/0162143 A1* | 8/2003 | Fischer et al. ................ 433/29 |
| 2003/0170586 A1* | 9/2003 | Cozean et al. ................ 433/29 |
| 2003/0186195 A1 | 10/2003 | Comfort et al. |
| 2003/0215766 A1* | 11/2003 | Fischer et al. ................ 433/29 |
| 2003/0218880 A1 | 11/2003 | Brukilacchio |
| 2003/0219693 A1* | 11/2003 | Cao ............................ 433/29 |
| 2003/0219694 A1 | 11/2003 | Bianchetti et al. |
| 2003/0235800 A1* | 12/2003 | Qadar ......................... 433/29 |
| 2004/0029069 A1* | 2/2004 | Gill et al. ..................... 433/29 |
| 2004/0033033 A1 | 2/2004 | Hoshino et al. |
| 2004/0043351 A1* | 3/2004 | Logan et al. ................. 433/29 |
| 2005/0136373 A1* | 6/2005 | Fischer et al. ................ 433/29 |
| 2005/0158687 A1* | 7/2005 | Dahm ......................... 433/29 |

OTHER PUBLICATIONS

GC America, Inc., "Curing Modes for Today's and Tomorrow's VLC Dental Materials" Lit. Code 640001-0202, 2002.

* cited by examiner

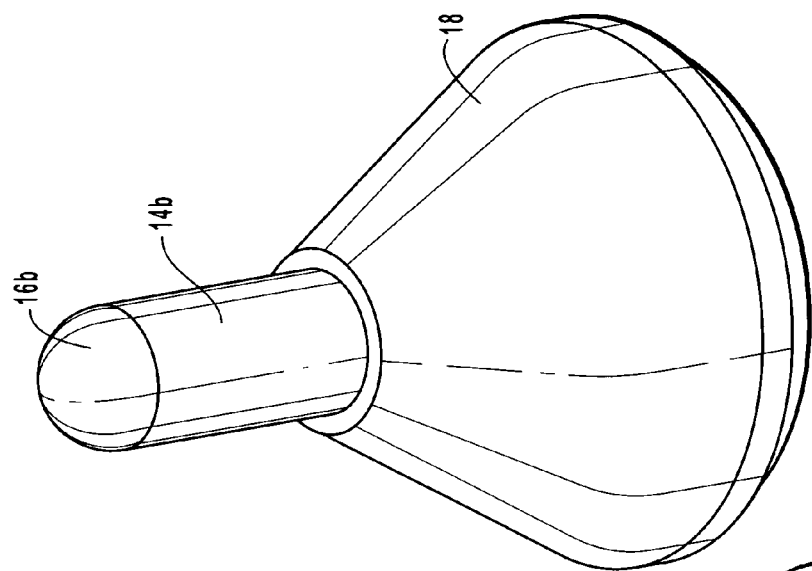
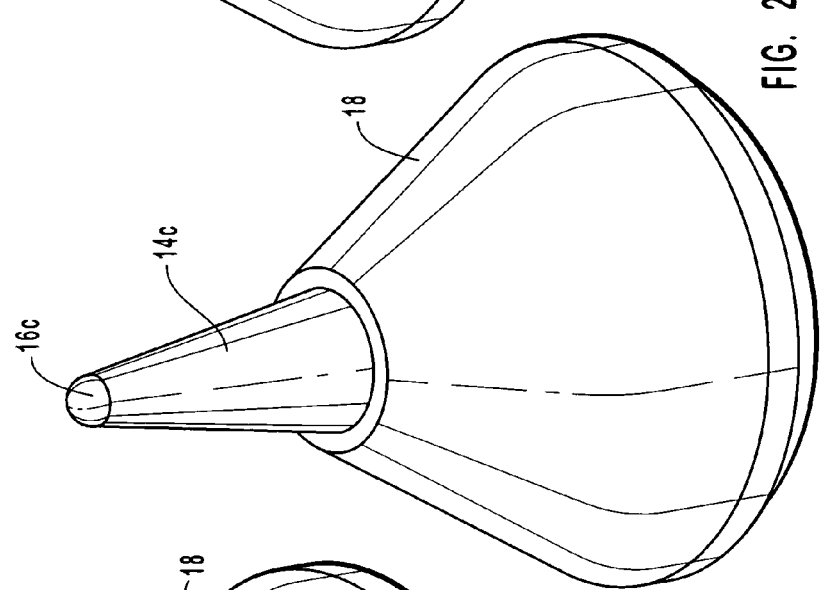
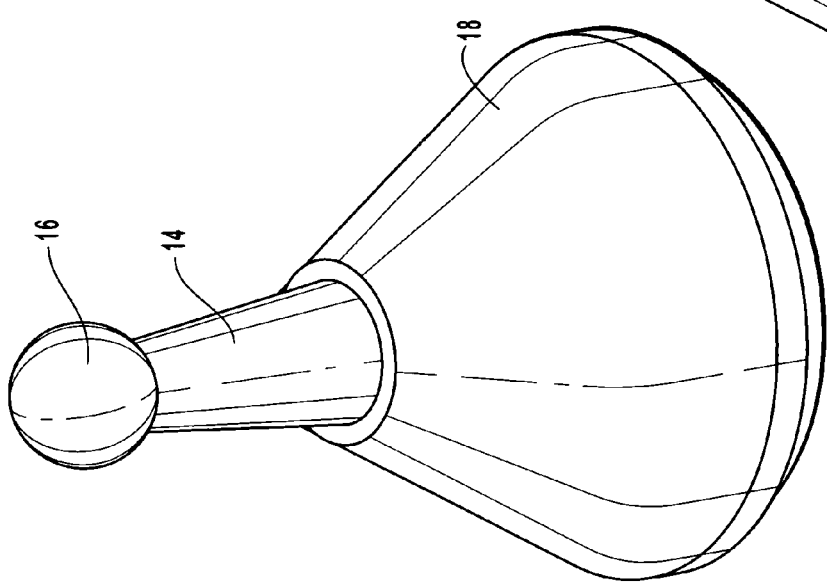

BALL LENS FOR USE WITH A DENTAL CURING LIGHT

BACKGROUND OF THE INVENTION

1. The Field of the Invention

The present invention relates to the field of dentistry, particularly to dental light curing devices used to cure light curable compositions used in dental restoratative procedures. More particularly, the invention is in the field of lenses that are attached to light curing devices and methods of use.

2. The Relevant Technology

Light curing devices are employed to polymerize and cure light curable compositions in a variety of industries. Light curing devices include a light source which emits light energy for curing a light curable composition. In the field of dentistry, for instance, light curing devices are often employed to polymerize and cure light curable compositions, such as light curable composites, adhesives, resins, and other polymerizable compositions containing photoinitiators.

By way of example, a light curable composite is often employed to fill a dental cavity preparation. Once the dental preparation has been cleaned and/or etched in preparation to filling, a layer of light curable composite is delivered to the area to be filled. Because the wavelengths used to cure the composition generally do not penetrate deeply, a series of thin layers are applied, curing each layer before applying the next.

In the course of placing filling material in between teeth, a matrix form, typically made of metal or plastic, is used. With resin restorations, it can be difficult to have the filling make tight contact with the adjacent tooth. Tight contacts are important or the patient will pack food debris in between the teeth. This is not only a nuisance, but can lead to further complications. Additionally, it is important that the contours between the teeth be anatomically correct, particularly with appropriate convexities. This is important to maintain healthy gum tissue below the contact area, but it is also important to support the biting surface of the filling correctly and prevent breakage of the filling.

In view of the foregoing, there is an ongoing need to provide improved apparatus and methods for fabricating and filling dental preparations.

BRIEF SUMMARY OF THE INVENTION

The present invention is directed to a ball lens to be used with a light-emitting device and related methods for filling a dental preparation with a light-curable filling material. The ball lens and related method allows a dental practitioner to establish a tight contact as each increment of resin filling material is constructed. At the same time, it allows the dental practitioner to develop an anatomically correct convexity in the proximal filling.

The ball lens includes a connector body configured to couple or attach to a light-emitting device, an elongate light guide extending from the connector body, and a light transmitting ball at an end of the light guide distal to the connector body. The connector body captures at least some of the light emitted by the light source of a light-emitting device during use. The ball lens allows a dental practitioner to hold a matrix band against an adjacent tooth prior to and/or while incrementally curing the light curable composition.

The lens may be integrally connected to a light-emitting device, or it may be configured to be removably attached to a light-emitting device so as to capture at least some of the light emitted by the light source of the light-emitting device. The type of connection between the ball lens and the light-emitting device may include a snap fit, a friction fit, a threaded fitting, a bayonet coupling, or other similar couplings.

In use, a layer of a light curable composition is applied to a dental preparation. The ball lens is used to hold a matrix band against an adjacent tooth prior to and/or while incrementally curing the composition. Additional layers of composition may be applied and cured while holding the matrix band against the adjacent tooth until the dental preparation is filled as desired. Using the ball lens to hold the matrix band against the adjacent tooth results in a filling making tight contact with the adjacent tooth while having an anatomically correct convexity.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 2A–2C illustrate alternative elongate light guides and light-emitting balls that may be used in the lenses of FIGS. 1A–1C;

DETAILED DESCRIPTION OF THE PREFERRED EMBODIMENTS

I. Introduction and Definitions

As used herein, the term "light-emitting device" includes any dental light device that generates light, whether using a bulb, plasma arc light, laser diode, an LED, a plurality of LEDs, or other light source. It also includes any dental device that emits (even though it may not generate) light, such as a fiber optic light guide. A "light-emitting device" may comprise all or part of a "dental curing light" or "device".

The term "footprint," as used herein, is generally made with reference to the cross-sectional shape of light emitted by a light-emitting device. The general shape and dimensions of a "footprint" of light can be identified by placing an object (e.g., a generally flat object) in front of a light source and observing the size and shape of the area illuminated by the light source.

The ball lens of the present invention includes a connector body that couples or attaches to a dental curing light so as to capture at least some of the light emitted by the light source, a light guide extending from the connector body through which light captured by the connector body can be channeled or transmitted, and a light-emitting ball at an end of the light guide distal to the connector body through which light can be emitted.

II. Exemplary Ball Lenses

Figure 1A:
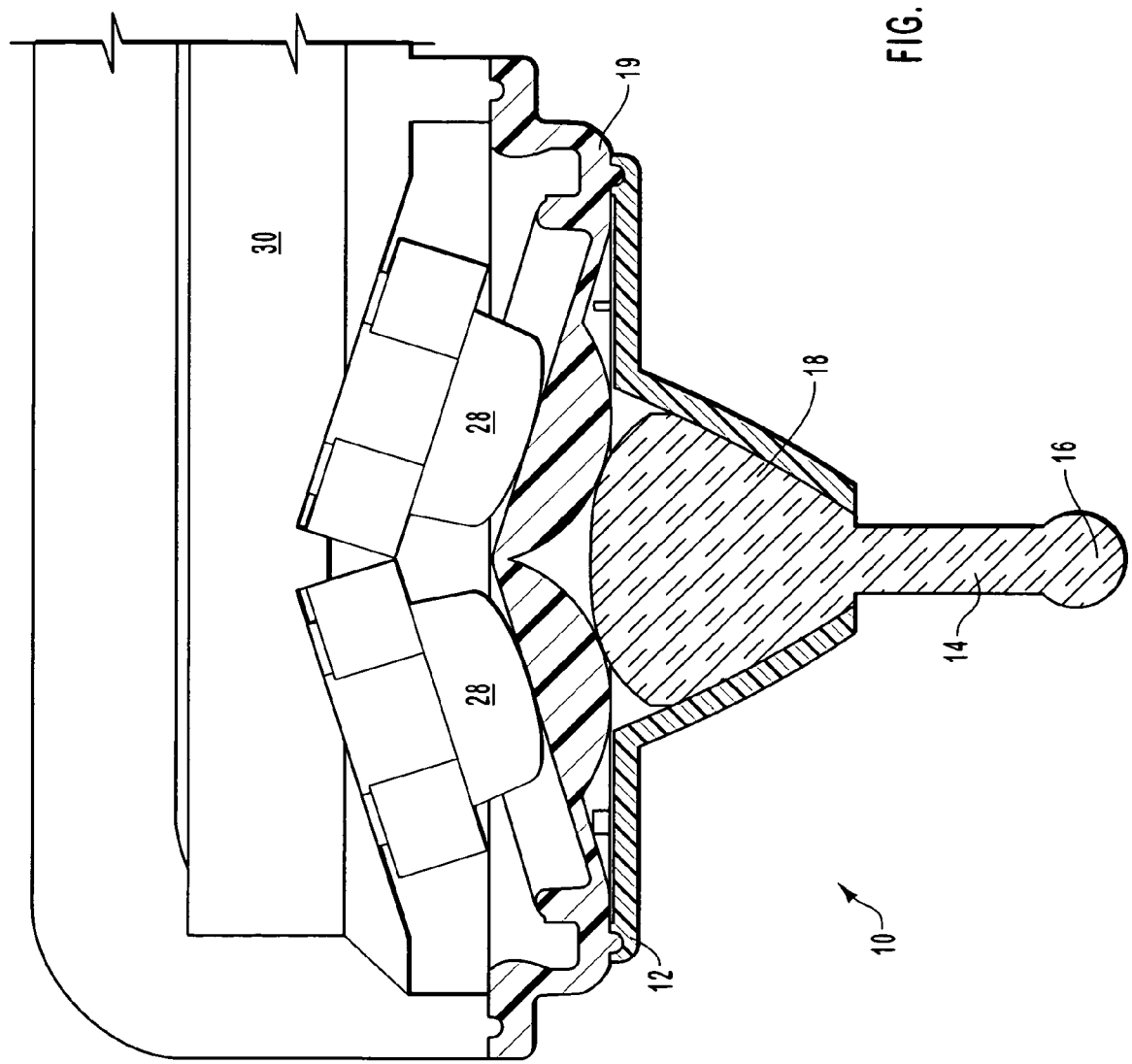
FIGS. 1A–1C illustrate exemplary embodiments of ball lenses according to the invention.

FIG. 1A illustrates an exemplary embodiment of a ball lens according to the present invention. Ball lens 10 includes a connector body 12, an elongate light guide 14 extending from the connector body 12, and a light-emitting ball 16 at an end of the light guide 14 distal to connector body 12. In addition, lens 10 includes an optional focusing lens 18 disposed within a hollow interior defined by body 12. The connector body 12 is configured to releasably attach the lens 10 to a light-emitting device 30. In the embodiment shown in FIG. 1A, the lens 10 is actually attached to an intermediate focusing lens 19, which is itself attached (integrally or releasably) to the light-emitting device 30. It will be understood that the intermediate lens 19 is optional such that the lens 10 can be attached directly to the light-emitting device 30 by any desired attachment means (not shown) known in the art. For example, the ball lens 10 may be attached to light-emitting device 30 by means of a snap fit, a press fit, a friction fit, a threaded coupling, a bayonet coupling, or any other type of coupling. Alternatively, the connector body 12 may be integrally attached to the light-emitting device (or intermediate lens).

Also illustrated in FIG. 1A is an array of two light sources 28, which are preferably light-emitting diodes (LEDs), but may include any kind of light source, including, for example, laser diodes, plasma arc lights, or various bulbs (such as halogen bulbs, incandescent bulbs, or fluorescent bulbs).

The connector body 12 may be opaque so as to block transmission of light energy through the connector body 12 so that curing light energy transmitted by the lens 10 has a pattern or footprint that is smaller than the footprint of light energy that would be emitted without an opaque connector body 12. Alternatively, the connector body 12 may be transparent so as to facilitate curing light being transmitted through the connector body 12.

Figure 1B:
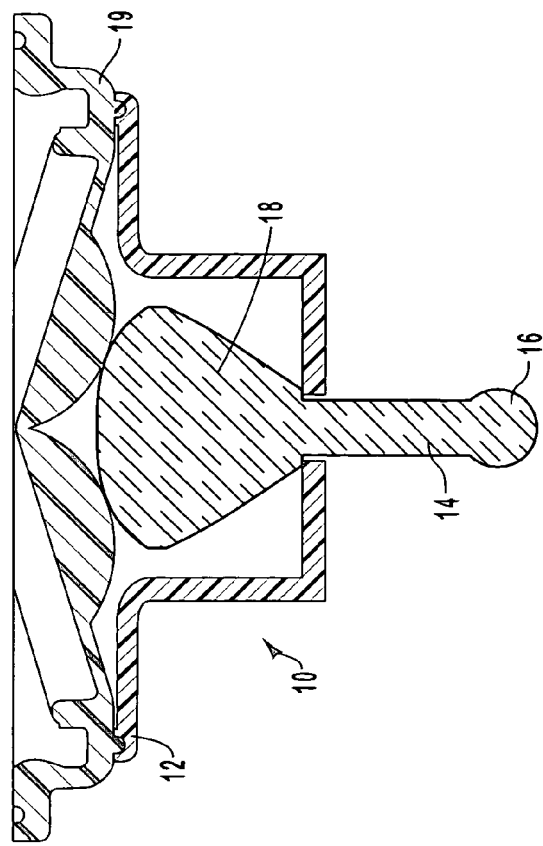
Figure 1C:
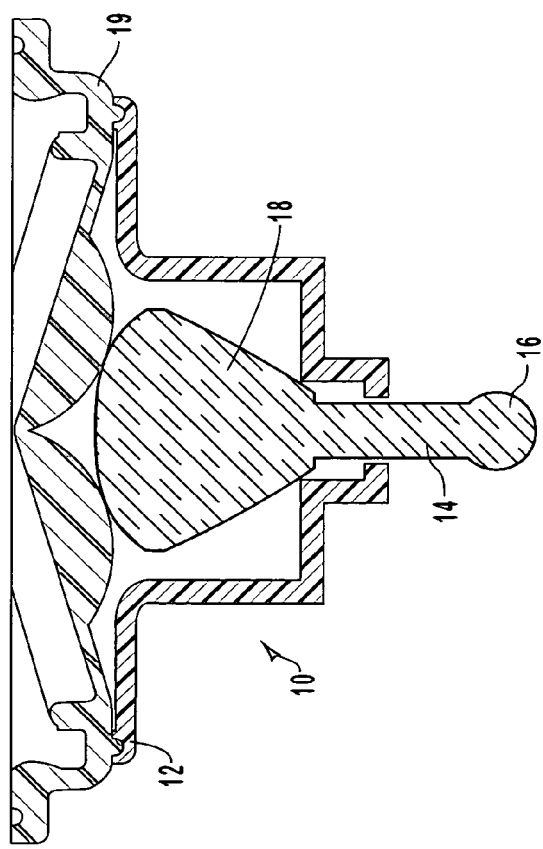

The connector body 12 may have various configurations. The conical connector body 12 of FIG. 1A is one exemplary configuration. Alternative conical configurations are illustrated in FIGS. 1B–1C. At least a portion of the connector body 12 may be flat. If all of it is flat, it will simply comprise a flat disk or disk-like structure (not shown) having an aperture through which the elongate light guide extends.

The elongate light guide 14 extends from connector body 12 and is transparent or translucent to curing light energy, which allows it pass through and be transmitted by light guide 14. Elongate light guide 14 may be hard or somewhat flexible, as desired. The elongate light guide 14 (along with the connector body, ball, and any optional focusing lenses) may comprise any desired transparent or translucent material. According to one embodiment it may be formed of acrylic, polyacrylic, polycarbonate, silicone, aluminum dioxide, sapphire, quartz, or glass. According to another embodiment, it may be formed of urethane, polyurethane, silicone, polyethylene, or any other material with suitable transmission characteristics with respect to curing light energy.

Lens 10 may also include one or more focusing lenses, such as focusing lens 18. The curing device shown in FIG. 1A also includes an intermediate lens 19 for focusing light before entering the ball lens 10. Focusing lens 19 helps to collimate the light that is emitted from the light-emitting device 30. Exemplary focusing lenses for use in focusing light energy emitted by a plurality of LEDs are described in detail in U.S. application Ser. No. 10/044,346, the disclosure of which is hereby incorporated by reference. After passing through lens 19, the light enters focusing lens 18 and is further collimated before exiting out of the ball lens 10 through elongate light guide 14 and light-emitting ball 16. Lenses 18 and 19 are optional, and the space they occupy in FIG. 1A could alternately be empty, allowing the curing light energy to simply enter lens 10 through the end coupled to light-emitting device 30 and exit through elongate light guide 14 and ball 16. If present, focusing lenses 18, 19, or other such lenses may be formed of any transparent material known and used in the art, such as glass or plastic.

According to one embodiment, the ball has a diameter ranging from about 1 mm to about 6 mm, and more preferably from about 2 mm to about 4 mm.

FIGS. 2A–2C illustrate a number of exemplary focusing lenses 18, elongate light guides 14, and light-emitting balls 16 having varying configurations. Each focusing lens, elongate light guide, and ball may be formed together as one integral piece, or may comprise separate pieces. FIG. 2A illustrates a focusing lens 18 and an elongate light guide 14*a* that has a tapered configuration. A light-emitting ball 16 is a disposed at the end of the tapered elongate light guide 14*a*. FIG. 2B illustrates a focusing lens 18, an elongate light guide 14*b*, and a light-emitting ball 16*b* disposed at the end of the elongate light guide 14*b*. Ball 16*b* has a diameter substantially equal to the diameter of cylindrical elongate light guide 14*b*. FIG. 2C illustrates a focusing lens 18, a tapered elongate light guide 14*c*, and a ball 16*c* disposed at the end of the tapered elongate light guide 14*c*. Ball 16*c* has a diameter substantially equal to the end diameter of tapered elongate light guide 14*c*.

Figure 3:
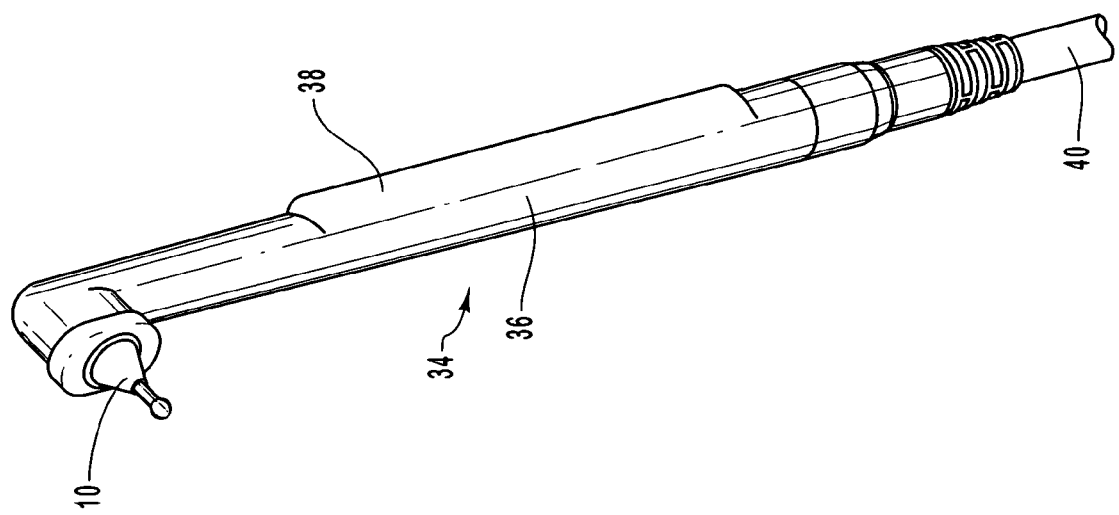
FIG. 3 illustrates a lens attached to a dental light curing device.

FIG. 3 illustrates one embodiment of a dental curing device 34 with a ball lens 10 attached thereto. Exemplary dental curing lights are disclosed in U.S. application Ser. No. 10/068,103, the disclosure of which is incorporated herein by reference. Dental curing device 34 has the general configuration of a standard dental hand piece. The shape of the body 36 is generally cylindrical, being defined by a circular cross-sectional shape. It will be appreciated, however, that the cross-sectional shape of the body 36 may be configured into other shapes, including, but not limited to, square, triangular, hexagonal, oval, rectilinear shapes, and combinations thereof. The body 36 may also include small or slight irregularities or protrusions such as protrusion 38, which may be configured with control buttons (not shown) for controlling the operation of the dental curing device 34. According to one embodiment, the dental light curing device also includes controls for controlling the intensity and/or duration of radiant energy from the light source.

The generally cylindrical shape of the body 36 enables a dental practitioner to comfortably hold the dental device 34 in various positions. The body 36 of the dental curing device 34 is also useful for enabling the dental practitioner to easily rotate and move the curing device 34 into various positions during a dental procedure.

As shown, the dental curing device 34 is also configured to be connected with a power cord 40 at a proximal end of the body 36. Although not shown, the power cord 40 operably connects the curing device 34 to a power supply (not shown) remotely located away from the curing device 34. The remote power supply may include an electrical wall receptacle, a battery pack, a generator, a transformer, or any other power supply suitably configured for providing an appropriate supply of power to the curing device 34 for illuminating the light source (not shown) of the curing device 34, which is disposed at the distal end of the dental device 34 under lens 10.

In one embodiment, the light source may include an LED configured to emit radiant energy that is suitable for curing light curable compositions. It will be appreciated, however, that a preferred light source may also include an LED array, a plurality of LEDs, or other light sources.

Lenses according to the invention may be attachable and detachable from the distal end of a light-emitting device using any known attachment means, such as with a snap fit, a friction fit, a press fit, a threaded coupling, a bayonet coupling, or any other type of coupling for enabling the lens or different types of lenses with different functionality to be interchangeably used with a light-emitting device according to need and preference.

Figure 4A:
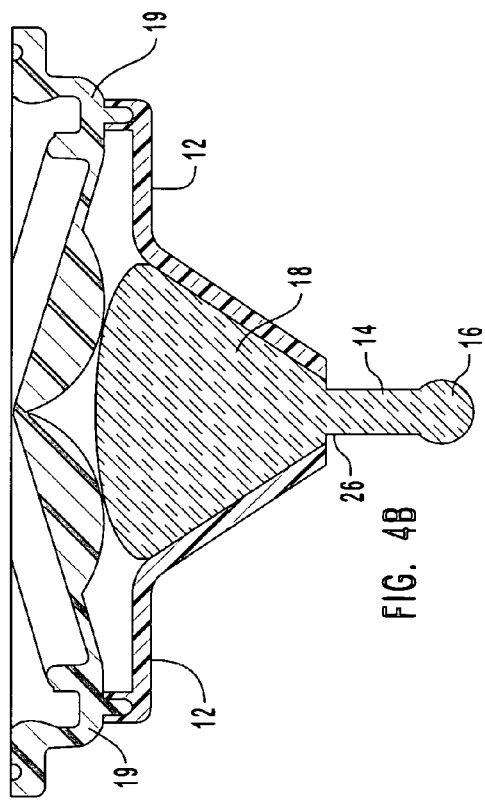
FIGS. 4A–4D illustrate several exemplary fittings for removably attaching a lens according to the invention to a focusing lens attached to a light-emitting device.
Figure 4B:
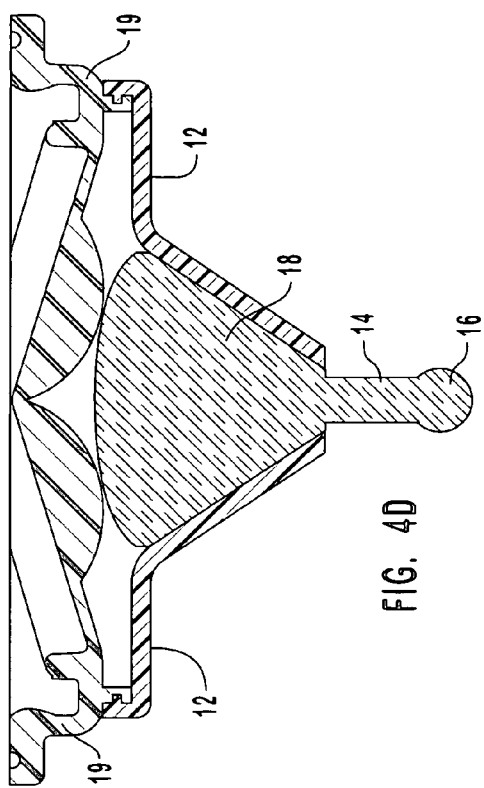
Figure 4C:
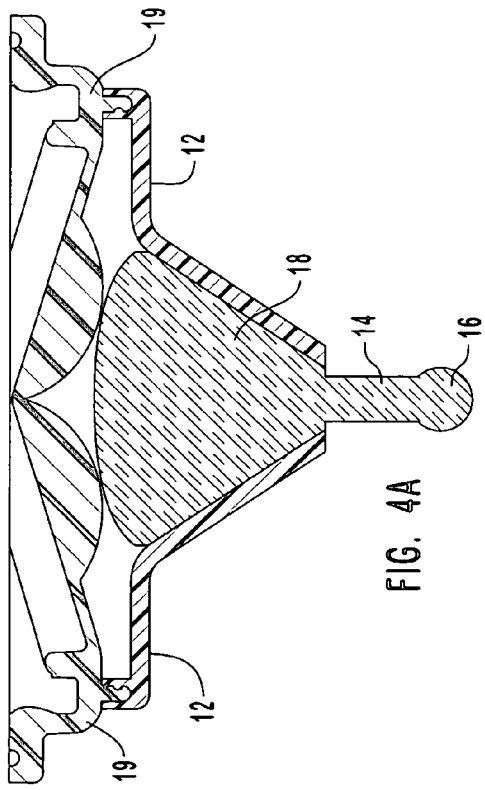
Figure 4D:
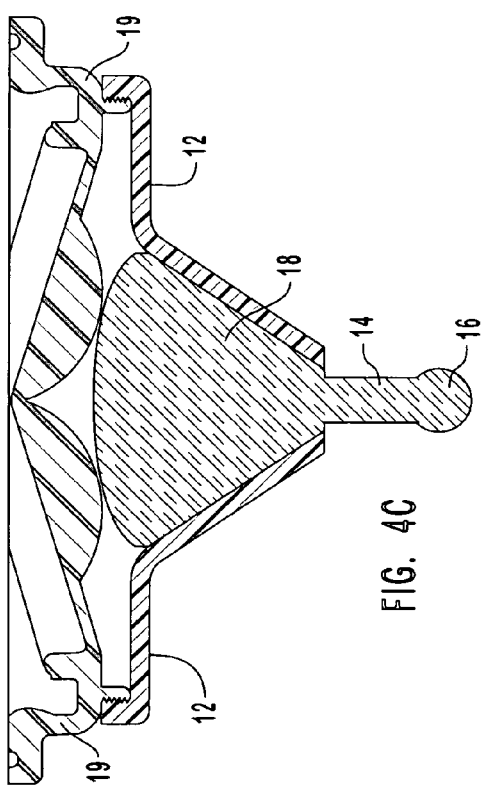

Several exemplary fittings between the connector body 12 and optional focusing lens 19 are illustrated in FIGS. 4A–4D. These same fittings could be used anywhere a detachable connection is desired (e.g. between focusing lens 19 and a light-emitting device, or between connector body 12 and a light-emitting device). FIG. 4A illustrates a snap fit arrangement. Focusing lens 19 includes a recess configured to retain a corresponding protrusion in connector body 12 in a snap-fit arrangement. FIG. 4B illustrates a friction or compression fit. Connector body 12 includes a recess configured to tightly receive a corresponding protrusion formed in focusing lens 19. FIG. 4C illustrates a threaded coupling. Connector body 12 and focusing lens 19 include corresponding grooves and raised threads, which raised threads are received in the corresponding grooves to threadably connect body 12 to focusing lens 19. FIG. 4D illustrates a bayonet coupling. Focusing lens 19 includes a recess configured to accept a corresponding protrusion formed in connector body 12. Alternatively, the lens may be integrally attached to either the lens 19 or a light-emitting device by, e.g., adhesive, welding, or other non-removable coupling.

Figure 5A:
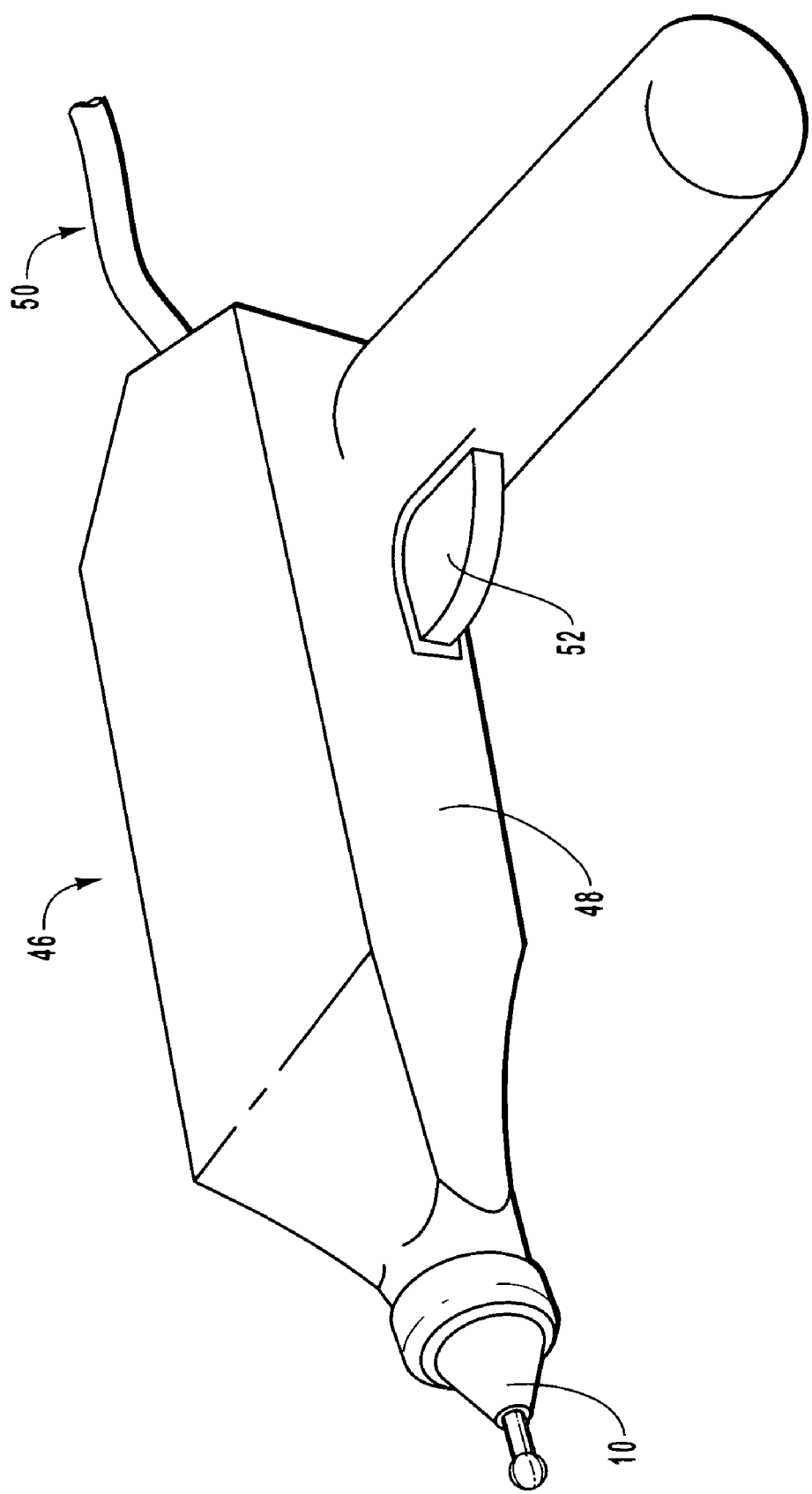
FIGS. 5A–5C illustrate alternative dental light curing devices with a lens attached thereto.

FIG. 5A illustrates an alternative dental light curing device 46 with a lens 10 attached thereto. Light curing device 46 is comprised of a body 48 coupled to a power source (not shown) by an electrical cord 50. Device 46 includes a trigger 52 or other activator to operate the device. The distal end of device 46 may include a light source (not shown) and corresponding structure configured to couple with lens 10. Light curing device 46 may use any kind of single or multiple light sources, including halogen bulbs, incandescent bulbs, fluorescent bulbs, laser sources, plasma arc lights, or light-emitting diodes (LEDs).

Lens 10 may be detachable from the distal end of the dental light curing device 46, such as with a snap fit, a friction fit, a threaded coupling, a bayonet coupling, or any other type of coupling for enabling the lens or different types of lenses with different functionality to be interchangeably used with the dental device 46 according to need and preference. Alternatively, the lens 10 may be integral with the distal end of the dental device 46, such as with an adhesive, by welding, or with other non-removable coupling.

Figure 5B:
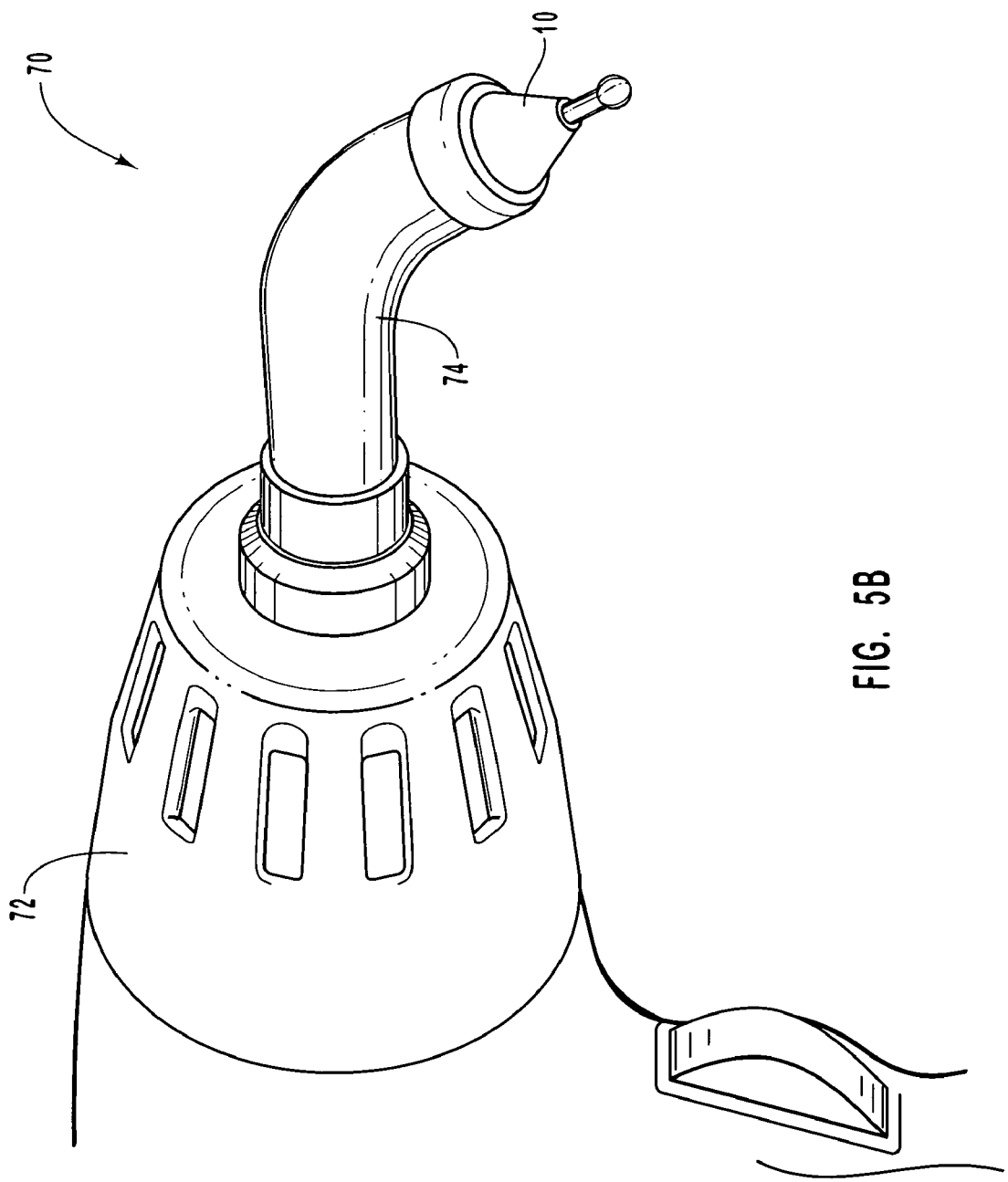

FIG. 5B illustrates a light curing system 70 comprising a light-emitting device 72 that includes a curved fiber optic light guide 74 configured so as to capture and transmit light generated by a light source (not shown) disposed within the light-emitting device 72. A lens 10 according to the invention is attached to a distal end of the fiber optic light guide 74, which comprises a "light-emitting device".

Figure 5C:
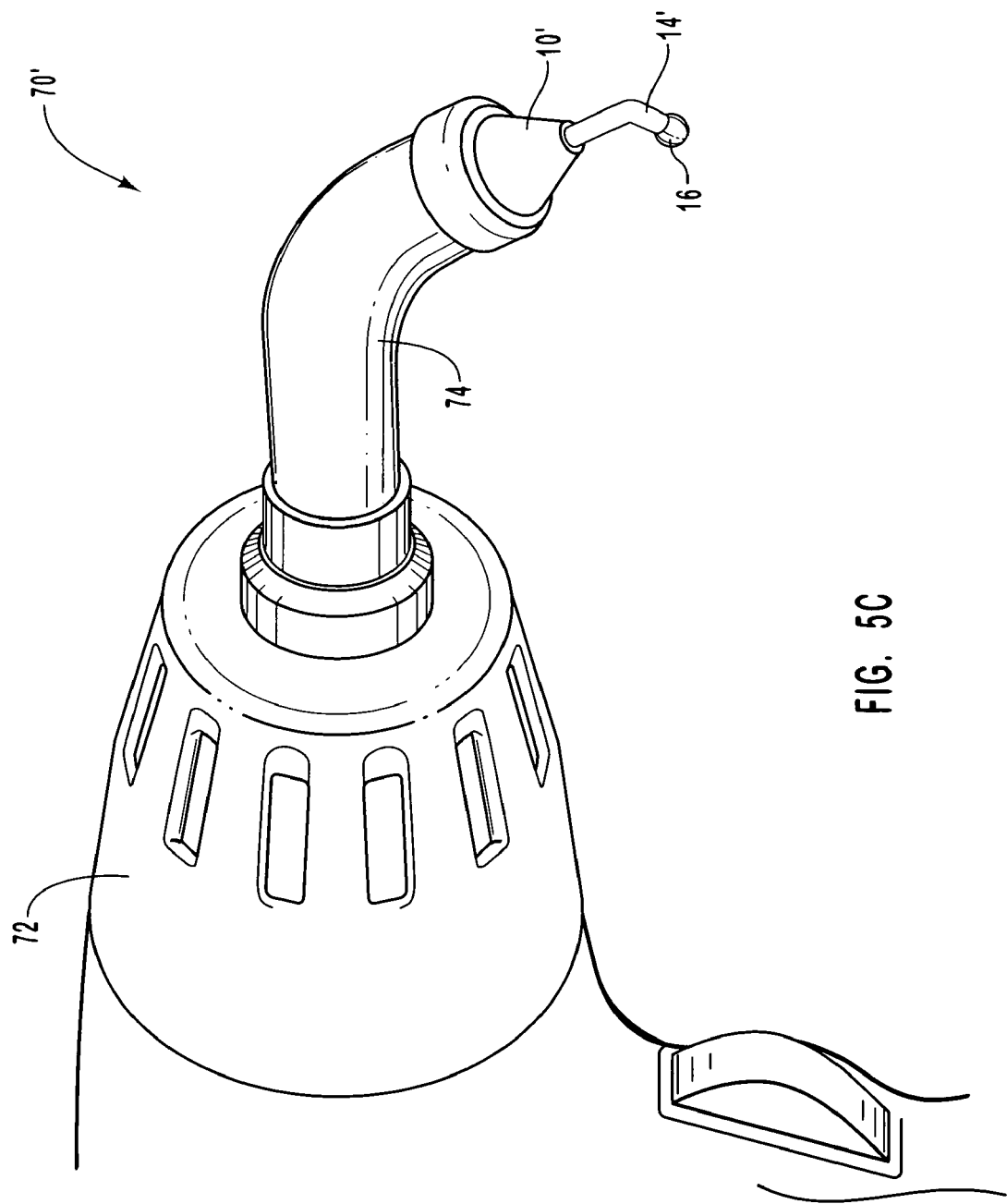

FIG. 5C illustrates a light curing system 70' comprising a light-emitting device 72 that includes a curved fiber optic light guide 74 configured so as to capture and transmit light generated by a light source (not shown) disposed within the light-emitting device 72. An alternative embodiment of a lens 10' having an elongate light guide 14' having a bend is attached to the distal end of the fiber optic light guide 74. An elongate light guide 14' having a bend may be useful and provide added convenience for working in hard-to-reach places, e.g., the back side of a tooth whose back side is not readily accessed using a lens with a straight elongate light guide.

The elongate light guide 14 can have any desired length, with lengths of 4–20 mm being preferred and lengths of 8–15 mm being more preferred. In one embodiment, the overall length of the elongate light guide 14' according to the invention is 11 mm overall, and 8 mm from the aperture of the connector body 12 from which the elongate light guide 14' extends to the bend.

III. Exemplary Method of Use

Figure 6A:
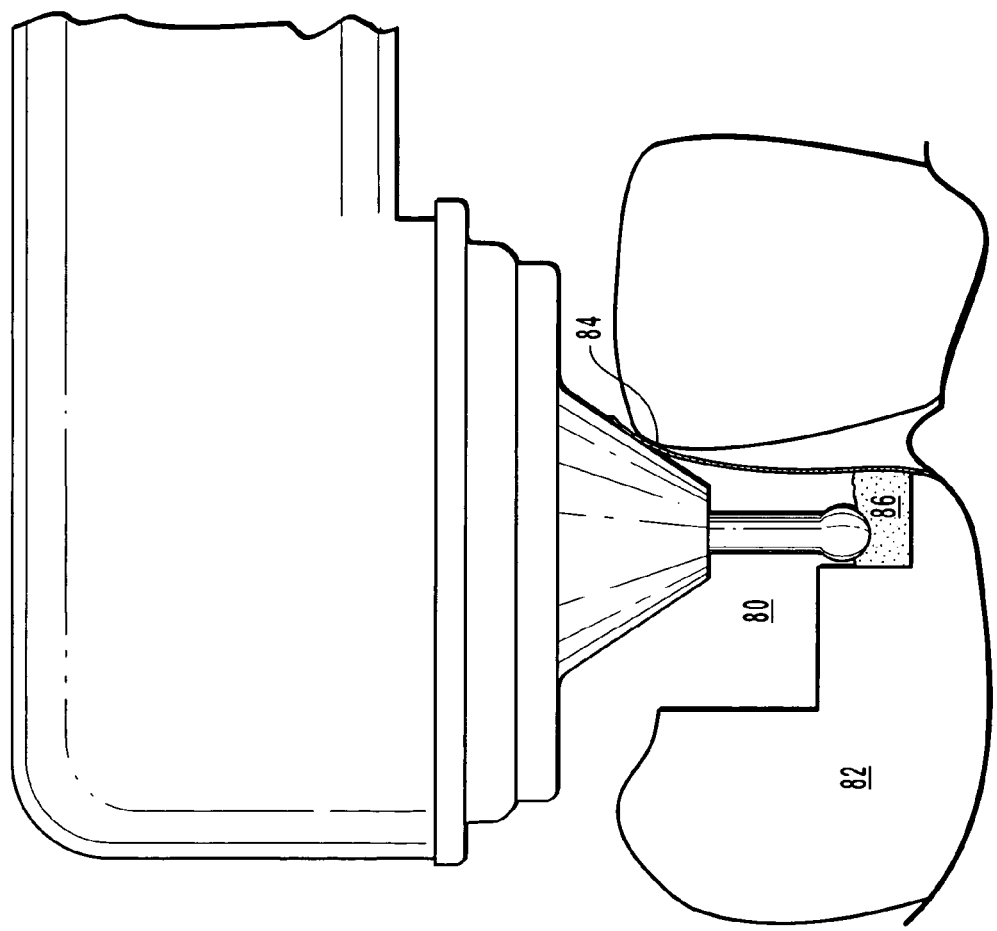
FIGS. 6A–6B illustrate a lens being inserted within a dental preparation.

FIG. 6A illustrates a lens 10 being used during filling of a dental preparation 80 of a tooth 82. The dental preparation 80 may represent any dental preparation, as known by those skilled in the art. As shown, the dental preparation 80 and tooth 82 may be surrounded by a matrix band 84 that may be used for providing form when filling the dental preparation 80. Matrix bands are well known to those of skill in the art. As shown, a layer of a light curable composition 86 is applied to the bottom of dental preparation 80. The elongate light guide 14 and ball 16 are sufficiently narrow so as to be insertable into the dental preparation 80. The dental practitioner may use the ball 16 to hold the matrix band 84 against the adjacent tooth prior to and/or while curing the layer of light curable composition 86.

Figure 6B:
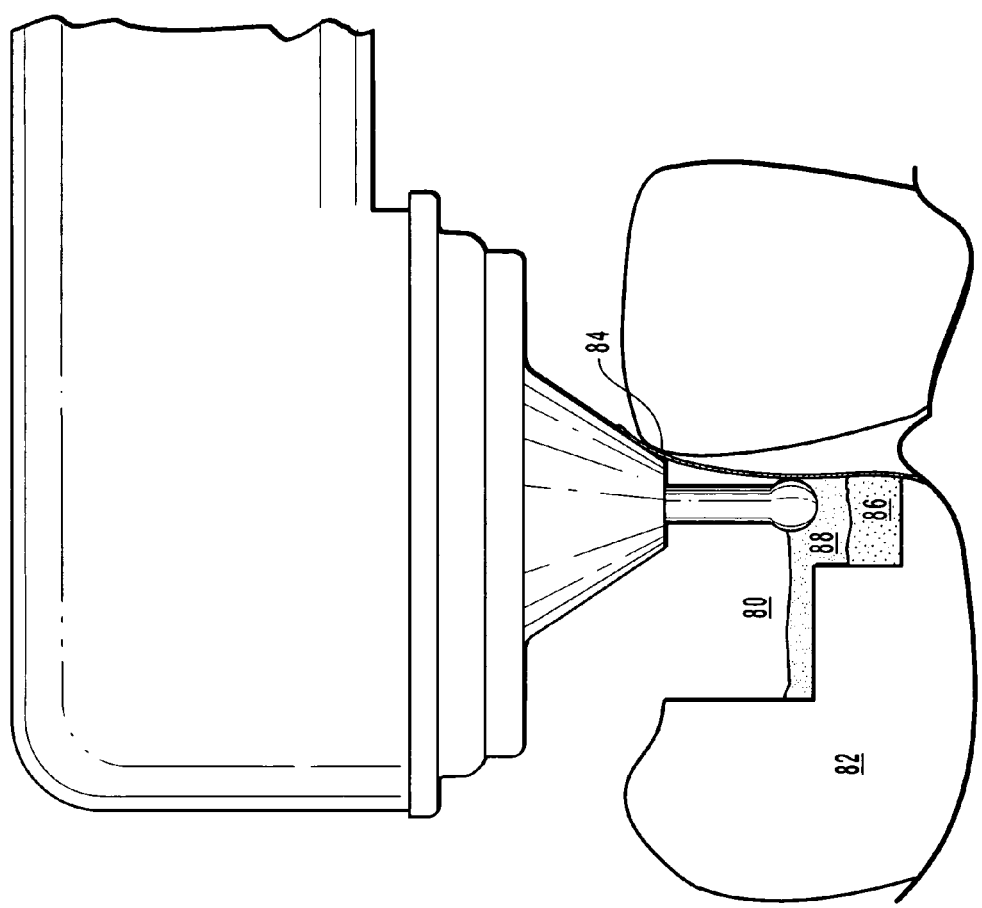

To minimize problems associated with polymerization shrinkage, light curable compositions may be applied in layers of about 2 mm or less. For deep dental preparations, a layer of composition 86 may be applied, the ball 16 may be used to hold the matrix band 84 against the adjacent tooth prior to and/or while curing the layer of light curable composition 86, and then a subsequent layer of light curable composition 88 may be applied. The ball 16 may be used to hold the matrix band 84 against the adjacent tooth while curing the layer of light curable composition 88 in the same manner, as illustrated in FIG. 6B. Additional layers of light curable composition are applied and cured in the same manner until the dental preparation 80 has been filled. Using the ball lens 16 to hold the matrix band 84 against the adjacent tooth results in a filling making tight contact with the adjacent tooth while having an anatomically correct convexity.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A lens for use with a light-emitting device when curing a dental composition within a dental preparation, comprising:
   a connector body that couples or attaches to a light-emitting device so as to capture at least some of the light emitted by the light source of the light-emitting device;
   a light guide extending from the connector body, said light guide having a proximal end adjacent to said connector body and a distal end, the proximal end of said light guide having a cross-sectional diameter that is no larger than half the cross-sectional diameter of said connector body in order to facilitate placement of said light guide within a dental preparation during a dental restoration procedure; and
   a ball or substantially rounded shape at the distal end of the light guide distal, said light guide being sufficiently rigid as to enable said ball or substantially rounded shape to hold a matrix band against a tooth adjacent to a dental preparation during use.

2. A lens as recited in claim 1, wherein said light-emitting device includes a light source comprising at least one LED or LED array.

3. A lens as recited in claim 1, wherein said light emitting device includes a light source comprising at least one of a halogen light, a plasma arc light, or a laser diode.

4. A lens as recited in claim 1, wherein said connector body is configured so as to releasably attach the lens to a light-emitting device.

5. A lens as recited in claim 4, wherein said connector body is configured so as to releasably attach the lens to a light-emitting device by a snap fit, a friction fit, a threaded coupling, or a bayonet coupling.

6. A lens as recited in claim 1, wherein said connector body is configured so that the lens is integrally attached to a light-emitting device.

7. A lens as recited in claim 1, wherein said light guide is substantially cylindrical.

8. A lens as recited in claim 7, wherein the ball has a diameter substantially equal to that of the cylindrical light guide.

9. A lens as recited in claim 1, wherein said light guide is tapered.

10. A lens as recited in claim 1, wherein the ball has a diameter ranging from about 1 mm to about 6 mm.

11. A lens as recited in claim 1, wherein the ball has a diameter ranging from about 2 mm to about 4 mm.

12. A lens as recited in claim 1, wherein said connector body has a hollow interior.

13. A lens as recited in claim 12, further comprising a focusing lens at least partially disposed within said hollow interior of said lens body.

14. A lens as recited in claim 13, wherein said focusing lens comprises a curved surface through which light enters and a light-emitting tip through which light energy exits into said elongate light guide.

15. A lens as recited in claim 13, wherein said focusing lens, said elongate light guide, and said ball are formed as one integral piece.

16. A lens as recited in claim 13, wherein said focusing lens, said elongate light guide, and said ball are formed from one or more of acrylic, polyacrylic, polycarbonate, silicone, aluminum dioxide, sapphire, quartz, glass, or other transparent or translucent material.

17. A lens as recited in claim 13, wherein said focusing lens, said elongate light guide, and said ball are formed from one or more of urethane, polyurethane, silicone, or polyethylene.

18. A light curing system for use in filling a dental preparation, the light curing system comprising:
   a light-emitting device that emits a footprint of light energy; and
   a lens adapted for use with the light-emitting device, the lens comprising:
      a connector body that couples or attaches to a light-emitting device so as to capture at least some of the light emitted by the light source of the light-emitting device;
      a light guide extending from the connector body, said light guide having a proximal end adjacent to said connector body and a distal end, said light guide being substantially cylindrical in order to facilitate placement of said light guide within a dental preparation during a dental restoration procedure; and
      a ball or substantially rounded shape at the distal end of the light guide distal to the connector body, said light guide being sufficiently rigid as to enable said ball substantially rounded shape to hold a matrix band against a tooth adjacent to a dental preparation during use.

19. A light curing system as recited in claim 18, wherein said light-emitting device includes a light source that comprises at least one of a halogen bulb, an incandescent bulb, a fluorescent bulb, a plasma arc light, or a laser diode.

20. A light curing system as recited in claim 18, wherein said light-emitting device includes a light source comprising at least one LED or LED array.

21. A light curing system as recited in claim 18, wherein said light-emitting device comprises a fiber optic light guide configured to capture and transmit light generated by a light source of said light-emitting device.

22. A method for curing a light curable composition within a dental preparation, comprising:
   providing a lens as recited in claim 1;
   applying a layer of a light curable composition to a dental preparation; and
   using said ball or substantially rounded shape to hold a matrix band against an adjacent tooth prior to and/or while incrementally curing said composition.

23. A lens for use with a light-emitting device when curing a dental composition within a dental preparation, comprising:
   a connector body that couples or attaches to a light-emitting device so as to capture at least some of the light emitted by the light source of the light-emitting device;
   a light guide extending from the connector body, said light guide having a proximal end adjacent to said connector body and a distal end; and
   a ball at the distal end of the light guide, wherein said ball has a diameter ranging from about 1 mm to about 6 mm, said light guide being sufficiently rigid as to enable said ball to hold a matrix band against a tooth adjacent to a dental preparation during use.

24. A lens as recited in claim 23, wherein said ball has a diameter ranging from about 2 mm to about 4 mm.

* * * * *

UNITED STATES PATENT AND TRADEMARK OFFICE
CERTIFICATE OF CORRECTION

PATENT NO. : 7,074,040 B2
APPLICATION NO. : 10/813306
DATED : July 11, 2006
INVENTOR(S) : Kanca It is certified that error appears in the above-identified patent and that said Letters Patent is hereby corrected as shown below:

Column 4
Line 34, before "disposed" remove "a"

Column 7
Line 18, after "light guide" remove "distal"

Column 8
Line 22, after "light guide" remove "distal to the connector body"
Line 62, after "4mm" change " : " to --.--

Signed and Sealed this

Third Day of July, 2007

JON W. DUDAS
*Director of the United States Patent and Trademark Office*